United States Patent
Van Dick (12)

(10) Patent No.: US 6,304,782 B1
(45) Date of Patent: Oct. 16, 2001

(54) METHOD OF REDUCING PHYSIOLOGICAL STRESS

(76) Inventor: Robert Van Dick, 10110 Loving Rd., Morganton, GA (US) 30560

( * ) Notice: Subject to any disclaimer, the term of this patent is extended or adjusted under 35 U.S.C. 154(b) by 0 days.

(21) Appl. No.: 09/401,761

(22) Filed: Sep. 23, 1999

(51) Int. Cl.$^7$ .................................................. A61N 1/32
(52) U.S. Cl. .............................. 607/45; 607/62; 607/76; 600/26
(58) Field of Search ............................ 607/2, 45, 62, 607/63, 76; 600/26, 549, 504

(56) References Cited

U.S. PATENT DOCUMENTS

| | | | |
|---|---|---|---|
| 3,900,020 | 8/1975 | Lock ................... | 125/2.2 C |
| 4,177,819 | * 12/1979 | Kofsky et al. ................ | 128/422 |
| 4,181,128 | 1/1980 | Swartz ................ | 128/207.21 |
| 4,305,402 | * 12/1981 | Katims ................ | 128/741 |
| 4,589,417 | 5/1986 | Eseifan et al. ................ | 128/422 |
| 4,644,955 | * 2/1987 | Mioduski ................ | 128/422 |
| 5,169,380 | * 12/1992 | Brennan ................ | 600/26 |
| 5,366,435 | * 11/1994 | Jacobson ................ | 600/13 |
| 5,620,463 | * 4/1997 | Drolet ................ | 607/3 |
| 5,643,173 | * 7/1997 | Welles ................ | 600/26 |
| 5,690,692 | 11/1997 | Fleming ................ | 607/50 |
| 5,759,158 | * 6/1998 | Swanson ................ | 600/508 |
| 5,817,141 | 10/1998 | Limori ................ | 607/76 |
| 5,817,142 | 10/1998 | Corder ................ | 607/76 |
| 5,848,985 | 12/1998 | Muroki ................ | 604/20 |
| 6,058,331 | * 5/2000 | King ................ | 607/62 |
| 6,108,580 | * 8/2000 | Greenspan et al. ................ | 607/74 |
| 6,267,721 | * 7/2001 | Welles ................ | 600/26 |

\* cited by examiner

*Primary Examiner*—Kennedy Schaetzle
(74) *Attorney, Agent, or Firm*—Baker, Donelson, Bearman & Caldwell

(57) ABSTRACT

Viral induced physiological stress is reduced by electronic diagnosis and treatment. A patient is slowly scanned with a sinusoidal signal over a frequency range within some 2,000 Hz to 6,000 Hz while stress level is monitored by fingertip thermal sensors. A 5 VAC source is used with a source impedance of between 8,000 and 12,000 ohms that is ungrounded. A fingertip temperature rise and peak is correlated with a therapeutic frequency. The patient is treated with a signal at the therapeutic frequency applied to the torso for a period of time sufficient to treat substantially all of the circulating blood in the patient. It is believed that the electrotherapy causes the viruses that induce the stress to resonate mechanically and become inactivated. By associating diagnosed frequencies with a prior diagnosed frequency, a diagnostic method is thus also provided.

12 Claims, No Drawings

METHOD OF REDUCING PHYSIOLOGICAL STRESS

TECHNICAL FIELD

This invention relates generally to methods for reducing physiological stress, and particularly to electrical methods for reduced physiological stress in humans that is induced by infectious agents.

BACKGROUND OF THE INVENTION

Viruses are submicrosopic, infectious agents that vary in size from 200 microns to 3,000 microns. Thus they are usually only viewed via electron microscopes. Because of their extremely small size it is extremely difficult, if not impossible, to utilize existing electronic test equipment for electrical measurements as to ascertain whether viruses have actually been broken up (inactivated) by physical resonance.

Everyone inherits the viruses of their mother from birth but they are dormant viruses as our immune systems stop virus multiplication by producing appropriate antibodies. Therefore, everyone has viruses in their blood at all times, either dormant and/or active. Blood, even though liquid, has electrical resistance and whole viruses in the blood affect the electrical resistance of the blood by being an impurity.

Heretofore electrical energy has been used to inactivate microorganisms such as viruses and bacteria. As early as the 1970's such was investigated at the Massachusetts Institute of Technology by Mitchell R. Swartz in activating Herpes simplex virus, in vivo. See for example U.S. Pat. No. 4,181,128. This involved the application of a solution that assumed an excited electron state when simultaneously subjected to light and in an electrical field. By adding hydrogen peroxide, hydroxyl free radical was formed by the Haber-Weiss reaction.

In 1995 Dr. Hulda Regehs Clark published a book entitled "The Cure for all Diseases." It disclosed that the application of electrical energy at 30 kHz could succeed in killing viruses, bacteria, parasites, toxins and molds.

In U.S. Pat. No. 5,690,692 a precise frequency synthesizer was disclosed for generating signals at 0.00004 Hz to 3 MHz as a square wave with a 50% duty cycle. The signal was used to inactivate microorganisms and viruses in mammals, it being recognized that every microorganism has its own specific molecular oscillation pattern. By subjecting a microorganism to a specific precise electrical frequency signal, it was possible to inactivate or kill the organism without effecting other microorganisms or tissues. This was followed soon by the application of electric energy at between 100 KHz and 900 KHz as described in 1998 in U.S. Pat. No. 5,690.692.

Although it has been recognized that electrical energy can be effectively employed in inactuating certain microorganisms, that approach has yet to be shown effective in reducing human physiological stress induced by viruses and bacteria and other micro and submicro organisms.

Techniques used to reduce human psychological stress have included pure mediation and mental exercises associated with electronic bio-feedback instruments coupled by sensors attached to the skull that monitor alpha and theta brain waves. More recently physiological stress has been treated by merely positioning a subject within a weak electromagnetic field. This protocol is discussed in U.S. Pat. No. 5,461,829. These methods however have not been directed to a common cause of such stress, that is to disease.

It thus is seen that although microorganisms have been known to be inactivated by the application of electrical energy and that physiological stress has been known to be alleviated also by electrical energy, it has not been known how to alleviate such stress by treatment of microorganisms and submicroorganisms. Were such an approach to be found effective, the dual benefit of reducing both stress and its biological cause could be achieved since a nexus between such stress and biological cause has long been recognized.

SUMMARY OF THE INVENTION

It has now been discovered that disease induced physiological stress can be effectively treated by electro-therapy applied directly to the in vivo organic agent. The application of a sinusoidal electric wave at a frequency within the range of 2000 Hertz and 6000 Hertz, at less than 180 micro amperes current, has been found to be effective in reducing disease induced physiological stress in humans. The specific frequency employed is within 5 Hz of a frequency within that range that is accompanied by physiological stress reduction in the patient. It is believed that this application causes the infectious microorganism to resonate mechanically and, in doing so, become inactivated and effectively destroyed as an organic agent. The specific frequency thus is tailored to the specific active microorganism. This is determined by slowly sweeping the subject with the same electric wave over the frequency range and determining the frequency that mechanical resonance occurs by a correspondent observed reduction in physiological stress. This observation is preferably made by finger tip temperature monitoring.

DETAILED DESCRIPTION

The electro therapy is applied across the upper torso, preferably with electric contacts applied to the skin of fingers, hands, wrists, arms or the armpits for a period of time sufficient to be applied to most of the subject's circulating blood. The contacts about opposite sides of the torso are coupled to a 5 volts peak-to-peak AC signal source that provides 180 microamps or less current with a sinusoidal wave form at a frequency of 2,000 Hz to 6,000 Hz. This signal amplitude preferably varies no more that ±15%. The source impedance of the signal generated is between 8,000 and 12,000 ohms and is floating, i.e. not grounded, to avoid any stray 60 Hz signals being mixed with its generated signal. RMS current levels increase from 40 microamperes initially to 125 microamperes during a treatment session. One session is typically of some 20 minute duration. Successive sessions are spaced apart some 4–7 days. The frequency sweep is conducted very slowly, at a rate no greater than 1-½ Hertz per second, and preferably at a rate of ½ to 1 Hertz per second.

The initial diagnostic frequency sweep is made very slowly until a rise in fingertip temperature is detected as with thermal measuring equipment having a temperature resolution capability of 0.01° F. A peak in temperature rise occurs within some 50 seconds. By the end of the first 10 seconds sixty percent of the rise to peak occurs. Scanning may detect multiple peaks during the sweep. This apparently indicates the presence of different viruses that induce different diseases. In that case the one of most immediate medical concern is selected for treatment if its correspondent frequency is already known. If not a trial and error approach may be taken in determining the priority of treatment frequencies. Preferably the initial treatment session immediately follows therapeutic frequency identification. However, the first treatment session may, of course, be given at another time and place.

Case History One

A patient diagnosed with meningitis was treated with four 22-minute sessions at a frequency of 3,511 Hz. This frequency had been identified by a peak in observed stress reduction during a slow frequency sweep. Stress levels were observed by fingertip temperature measurements. Following the fourth session no further meningitis symptoms were found to be present in the subject and physiological stress was greatly alleviated.

Case History Two

A patient with a 15-year history of bi-monthly shingles skin eruptions was treated with five 18-minute exposure spaced six days apart. A frequency of 3,945 Hz was applied after having been identified by a slow frequency sweep scan. Following this treatment protocol the monthly shingles outbreak appearances were found to have lessened dramatically from thousands of small skin eruptions every other month to some five small skin eruptions bi-monthly. A substantial reduction in physiological stress was also discerned to have occurred as measured by fingertip temperature comparisons.

Case History Three

A patient diagnosed with tuberculosis was treated with four 22-minute exposure sessions spaced five days apart. Treatment was performed at 3,475 Hz which had been identified by a slow sweep of frequencies. Following the fourth session, the subject's tuberculosis symptoms were no longer present and physiological stress was greatly reduced.

The effectiveness of the new treatment has been demonstrated both subjectively, by patient testimonials, and objectively by fingertip temperature changes. Finger tip temperatures decrease, caused by blood withdrawal, is well recognized as indicative of an increase in physiological stress. Conversely, a temperature increase is indicative of a lessening in such stress. This is conventionally observed with thermal sensors attached to the subject's finger tips in a constant temperature environment. Alternative extremity sites include the toes, ears and nose tip which are known sites where blood flow circulation increases in adrenal triggered response to stress reduction.

The underlying disease symptoms were also objectively found to have abated too. For examples, this was observed in a decrease in fatigue and malaise in the meningitis case, a virtual elimination of shingles outbreaks in the shingles patient and by an improved blood count with the tuberculant. Microorganisms and submicroorganisms inactivation confirmation is being pursued but has to date been hampered by the inability to disseminate between active and inactive viruses with most available test methods and equipment. Confirmation that inactivation or destruction has resulted from resonance, i.e. from being shaken apart, will of course be more difficult.

It is believed that by slowly scanning a patient at frequencies of between 2,000 and 6,000 Hz, the mechanical resonant frequency, or its harmonic, is detected by stress reduction peaking during the slow sweep. By correlating this with conventional diagnoses, this sweep itself yields a diagnostic means. In other words, once a frequency has been determined to be effective on one virus, it may serve as a reference frequency for future diagnostic use with other patients. Of course, such classification and disease diagnosis by name is not absolutely necessary since the waveform frequency used in the treatment is virtually the same as that identified in the observant peak in fingertip temperature rise. How both bacteria and viruses can resonate within the same band or range of frequencies is not understood, the former being orders of magnitude larger than the other. That answer may, of course, lay in the presence of harmonics or in it still being the viruses within their living hosts which are being inactivated. Also unconfirmed is the reason why only the viruses resonate and not other healthy bodies of finite size such as blood cells. But again, this is apparently attributable to the lower current and voltage level and the signal frequency range, cells and bacteria being so much larger than viruses.

The therapeutic signal frequency is applied within 5 Hz of the diagnostic frequency observed during patient scan. Physical or mechanical resonance as the operative factor present is consistent with the fact that patient resistance has been found to decrease (by a detected increase in microampere current) during treatment sessions with blood being, of course, a major component of the electrical load.

It thus is seen that a method of reducing physiological stress has now been found with a virology nexus. Although the method has been described in its preferred form, it should be understood that variations may be made thereto without departure from the spirit and scope of the invention as set forth in the following claims.

What is claimed is:

1. A method of reducing disease induced physiological stress in a patient wherein the patient is slowly scanned with diagnostic substantially sinusoidal alternating current in a range that is between 2,000 Hz and 6,000 Hz and detecting a physiological stress reduction peak at a frequency within that range, and applying therapeutic alternating current to the patient at a frequency approximately equal to the detected frequency a period of time sufficient to reduce physiological stress in the patient.

2. The method of claim 1 wherein the stress reduction peak is detected by monitoring the temperature of an extremity of the patient.

3. The method of claim 2 wherein the stress reduction peak is detected by fingertip temperature monitoring.

4. The method of claim 1 wherein the patient is scanned at a scan rate of less than one and one half Hertz.

5. The method of claim 1 wherein the therapeutic current is applied to substantially all of the patient's blood.

6. The method of claim 1 wherein the patient is scanned over the frequency range of 2,000 Hz to 6,000 Hz.

7. An electrotherapeutic method of reducing physiological stress and inactivating its viral cause in a patient wherein a treatment signal is determined by scanning the patient with substantially sinusoidal alternating current over a frequency range that is within the range of 2,000 to 6,000 Hz and detecting the frequency at which physiological stress reduction occurs, and applying the determined treatment frequency signal to the patient for a time sufficient to reduce the physiological stress and to inactivate its viral cause.

8. The method of claim 7 wherein the frequency at which physiological stress reduction occurs is detected by an accompanying rise in temperature of a body extremity.

9. The method of claim 8 wherein the stress reduction peak is detected by fingertip temperature monitoring.

10. The method of claim 7 wherein the patient is scanned at a scan rate of less than one and one half Hertz.

11. The method of claim 7 wherein the patient is scanned over the frequency range of 2,000 Hz to 6,000 Hz.

12. The method of claim 7 wherein the treatment signal is applied to substantially all of the patient's blood.

* * * * *